United States Patent [19]

Möller et al.

[11] 4,136,165

[45] Jan. 23, 1979

[54] COSMETIC PREPARATIONS WITH ALKOXYBENZOIC ACID ESTERS AS INFLAMMATION INHIBITORS AND METHOD

[75] Inventors: Hinrich Möller, Dusseldorf; Hans-Joachim Thimm, Hilden, both of Germany

[73] Assignee: Henkel Kommanditgesellschaft auf Aktien, Dusseldorf-Holthausen, Germany

[21] Appl. No.: 789,844

[22] Filed: Apr. 22, 1977

[30] Foreign Application Priority Data

Apr. 23, 1976 [DE] Fed. Rep. of Germany ..... 26178176

[51] Int. Cl.² ............... A61K 7/44; A61K 31/235; A61L 23/00
[52] U.S. Cl. .................... 424/60; 424/308; 424/46; 424/47; 424/230; 424/233; 424/DIG. 13
[58] Field of Search ................. 424/60, 308

[56] References Cited

U.S. PATENT DOCUMENTS

| | | | |
|---|---|---|---|
| 1,627,342 | 5/1927 | Sabalitschka | 424/308 |
| 1,715,251 | 5/1929 | Sabalitschka et al. | 424/308 |
| 1,879,351 | 9/1932 | Lehmann | 424/308 |
| 2,041,874 | 5/1936 | Stockelbach | 424/60 |
| 2,102,712 | 12/1937 | Isermann et al. | 424/60 |
| 2,395,665 | 2/1946 | Isermann et al. | 424/60 |
| 2,523,316 | 9/1950 | McClenahan et al. | 424/308 |
| 2,568,760 | 9/1951 | Pearl | 424/60 |
| 2,609,323 | 9/1952 | Pearl | 424/308 |

FOREIGN PATENT DOCUMENTS

1492322  1/1970  Fed. Rep. of Germany ............. 424/60

Primary Examiner—Donald B. Moyer
Attorney, Agent, or Firm—Hammond & Littell

[57] ABSTRACT

Compositions for the treatment of inflammation of the skin containing from 0.01% to 10% by weight of an alkoxybenzoic acid ester of the formula

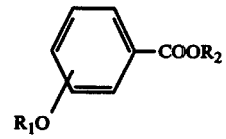

where $R_1$ is alkyl having 1 to 6 carbon atoms, and $R_2$ is alkyl having 1 to 8 carbon atoms, cyclohexyl, phenyl or benzyl, as inflammation inhibitor; as well as the method of skin treatment.

3 Claims, No Drawings

COSMETIC PREPARATIONS WITH ALKOXYBENZOIC ACID ESTERS AS INFLAMMATION INHIBITORS AND METHOD

The present invention relates to inflammation inhibitors for use in cosmetic preparations, particularly for use in agents for protection against, and the treatment of, sunburn, based on alkoxybenzoic acid esters.

OBJECTS OF THE INVENTION

An object of the present invention is the development of a cosmetic inflammation-inhibiting composition for the care of skin of warm-blooded animals consisting essentially of a cosmetic preparation selected from the group consisting of oils, water-in-oil emulsions, oil-in-water emulsions, mixed aqueous water-soluble lower alkanol solutions having at least 20% lower alkanols, and cosmetic powders, containing from 0.01% to 10% by weight of an alkoxybenzoic acid ester of the formula

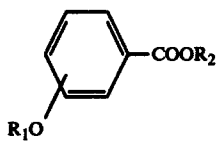

wherein $R_1$ is alkyl having 1 to 6 carbon atoms and $R_2$ is a member selected from the group consisting of alkyl having 1 to 8 carbon atoms, cyclohexyl, phenyl and benzyl, as an inflammation inhibitor, and from 0 to 10% by weight of ultraviolet filtering compounds.

Another object of the present invention is the development of a process for the care of the skin of warmblooded animals against topical inflammation comprising topically applying to the skin a safe but effective amount for the inhibiting of inflammation of a cosmetic inflammation-inhibiting composition consisting essentially of a cosmetic preparation selected from the group consisting of oils, water-in-oil emulsions, oil-in-water emulsions, mixed aqueous water-soluble lower alkanol solutions having at least 20% lower alkanols, and cosmetic powders, containing from 0.01% to 10% by weight of an alkoxybenzoic acid ester of the formula

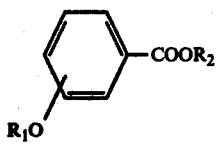

wherein $R_1$ is alkyl having 1 to 6 carbon atoms and $R_2$ is a member selected from the group consisting of alkyl having 1 to 8 carbon atoms, cyclohexyl, phenyl and benzyl, as an inflammation inhibitor, and from 0 to 10% by weight of ultraviolet filtering coupounds.

These and other objects of the present invention will become more apparent as the description thereof proceeds.

DESCRIPTION OF THE INVENTION

It has been found that alkoxybenzoic acid esters of the following general formula are eminently suitable as inflammation inhibitors in cosmetic preparations:

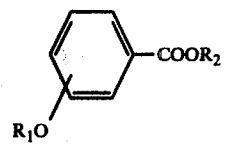

in which $R_1$ represents an alkyl having 1 to 6 carbon atoms, and $R_2$ represents an alkyl having 1 to 8 carbon atoms, a cyclohexyl, a phenyl or a benzyl.

More particularly, the present invention involves a cosmetic inflammation-inhibiting composition for the care of the skin of warm-blooded animals consisting essentially of a cosmetic preparation selected from the group consisting of oils, water-in-oil emulsions, oil-in-water emulsions, mixed aqueous water-soluble lower alkanol solutions having at least 20% lower alkanols, and cosmetic powders, containing from 0.01% to 10% by weight of an alkoxybenzoic acid ester of the formula

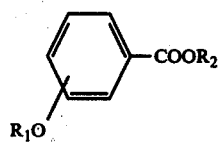

wherein $R_1$ is alkyl having 1 to 6 carbon atoms and $R_2$ is a member selected from the group consisting of alkyl having 1 to 8 carbon atoms, cyclohexyl, phenyl and benzyl, as an inflammation inhibitor, and from 0 to 10% by weight of ultraviolet filtering compounds; as well as a process for the care of the skin of warm-blooded animals against topical inflammation comprising topically applying to the skin a safe but effective amount for the inhibition of inflammation of a cosmetic inflammation-inhibiting composition consisting essentially of a cosmetic preparation selected from the group consisting of oils, water-in-oil emulsions, oil-in-water emulsions, mixed aqueous water-soluble lower alkanol solutions having at least 20% lower alkanols, and cosmetic powders, containing from 0.01% to 10% by weight of an alkoxybenzoic acid ester of the formula

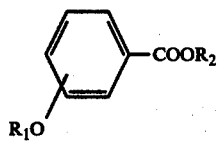

wherein $R_1$ is alkyl having 1 to 6 carbon atoms and $R_2$ is a member selected from the group consisting of alkyl having 1 to 8 carbon atoms, cyclohexyl, phenyl and benzyl, as an inflammation inhibitor, and from 0 to 10% by weight of ultraviolet filtering compounds.

The alkoxybenzoic acid esters are particularly important as inflammation inhibitors in cosmetic agents for protection against, and the treatment of, sunburn. When used in cosmetic agents for preventing sunburn, the inflammation-inhibiting esters in accordance with the present invention are used preferably in combination with ultraviolet filtering compounds, for example, conventional ultraviolet filtering compounds, such as aminobenzoic acid esters, cinnamic acid esters and their derivatives, salicylic acid esters and salts, anthranilic acid esters, benzophenones, aminocoumarins, benzimidazoles, etc.

The alkoxybenzoic acid esters to be used, in accordance with the present invention, as inflammation inhibitors, can be produced by processes known per se. By way of example, they can be obtained from the corresponding alkoxybenzoic acids and alcohols by esterification in the presence of a water-binding agents, such as sulfuric acid, or by azeotropic removal of the water formed. A further possibility of manufacturing the products to be used in accordance with the present invention resides in the alcoholysis of the corresponding carboxylic acid chlorides.

The alkoxybenzoic acid esters to be used in accordance with the present invention are, for example, methyl anisate (p-methoxybenzoate)
ethyl anisate
propyl anisate
isopropyl anisate
butyl anisate
isobutyl anisate
sec. butyl anisate
tert. butyl anisate
1-pentyl anisate
2-pentyl anisate
3-pentyl anisate
2,2-dimethyl-propyl anisate
hexyl anisate
cyclohexyl anisate
heptyl anisate
octyl anisate
2-ethylhexyl anisate
benzyl anisate
phenyl anisate
ethyl m-methoxybenzoate
propyl m-methoxybenzoate
isopropyl m-methoxybenzoate
2-ethyl-hexyl m-methoxybenzoate
methyl o-methoxybenzoate
ethyl o-methoxybenzoate
2,2-dimethylpropyl o-methoxybenzoate
benzyl o-methoxybenzoate
ethyl p-ethoxybenzoate
propyl p-ethoxybenzoate
isopropyl p-ethoxybenzoate
tert. butyl p-ethoxybenzoate
ethyl p-propoxybenzoate
propyl p-propoxybenzoate
2-ethyl-hexyl p-propoxybenzoate
ethyl p-isopropoxybenzoate
ethyl p-butoxybenzoate
ethyl p-tert.-butoxybenzoate
ethyl p-(2,2-dimethylpropoxy)-benzoate
ethyl p-hexyloxybenzoate, etc.

The compounds to be used in accordance with the present invention are colorless, crystalline or liquid substances which are distinguished by a good inflammation-inhibiting effect, and with satisfactory physiological compatibility, particularly with respect to the skin.

When used in cosmetic agents for protection against the sun and which serve to prevent sunburn, the alkoxybenzoic acid esters to be used in accordance with the present invention are preferably used in combination with ultraviolet filtering compounds, for example, conventional ultraviolet filtering coupounds, such as ethyl p-aminobenzoate
propyl p-aminobenzoate
butyl p-aminobenzoate
isobutyl p-aminobenzoate
monoglyceryl p-aminobenzoate
ethyl p-dimethylaminobenzoate
amyl p-dimethylaminobenzoate
ethyl p-diethylaminobenzoate
amyl p-diethylaminobenzoate
ethyl p-methoxycinnamate
ethyl p-aminocinnamate
ethyl p-dimethylaminocinnamate
menthyl salicylate
homomenthyl salicylate
ethyleneglycol monosalicylate
monoglyceryl salicylate
2-ethylhexyl salicylate
tert.-butyl salicylate
bornyl salicylate
phenyl salicylate
triethanolammonium salt of salicylic acid
menthyl anthranilate
bornyl anthranilate
3-ethoxyethyl p-methoxycinnamate
2-ethylhexyl p-methoxycinnamate
isopropyl p-acetamidocinnamate
2,2'-dihydroxy-4,4'-dimethoxy benzophenone
2-hydroxy-4-methoxybenzophenone
2-hydroxy-4-n-octoxy-benzophenone
4-phenyl-benzophenone
2-hydroxy-4-methoxy-benzophenone-5-sulfonic acid
isooctyl 4-phenylbenzophenone-2-carboxylate
7-ethylamino-4-methyl-cumarin
7,8-dihydroxy-cumarin
6,7-dihydroxy-cumarin
7-hydroxy-cumarin
4-methyl-7-hydroxy-cumarin
2-phenylbenzimidazole-5-sulfonic acid
sodium 3,4-dimethoxyphenylglyoxylate
butylbenzalacetone
benzalacetophenone
3-benzylidine-D,L-camphor
3-(p-methylbenzylidine)-D,L-camphor
urocanic acid.

When used as substances for inhibiting inflammation, the alkoxybenzoic acid esters in accordance with the present invention can be incorporated in liquid, pasty or solid cosmetic preparations, such as aqueous/lower alkanolic solutions, aqueous/lower alkanolic suspensions, aqueous emulsions of both types, solutions in organic solvents, oils, salves, creams, pencils or powder. The preparations can serve a wide variety of purposes, such as toilet water having an inflammation-inhibiting effect, after-shave lotions, pencils or lotions against insect stings, after-shave powder, baby powder, baby creams or baby lotions, and particularly as aqueous, emulsion-like oily or pasty cosmetic preparations for protection against sunburn or for the treatment of sunburn.

When used in this manner as substances for inhibiting inflammation, the alkoxybenzoic acid esters, in accordance with the present invention, are used in amounts of from 0.01% to 10% by weight, preferably from 0.5% to 5% by weight, relative to the total preparation of the cosmetic composition. When the alkoxybenzoic acid esters in accordance with the present invention are used in agents for protection against sunburn in combination with ultraviolet filtering substances, the amounts of the ultraviolet filtering substances are from 1% to 10% by weight, preferably 2% to 6% by weight, relative to the total cosmetic composition agent for protection against sunburn.

The remainder of the cosmetic compositions of the invention comprise the conventional cosmetic constituents, such as emulsifiers and water for water-in-oil and oil-in-water emulsions, fatty substances, plant extracts, solvents, scents, thickeners, preservatives, finely dispersed inorganic and organic powders, such as talcum powder.

The incorporation of the alkoxybenzoic acid esters into the cosmetic compositions of the invention may take place in the known manner by simple stirring-in or dissolving. In addition to the alkoxybenzoic acid esters in accordance with the invention, the cosmetic preparations may contain the constituents normally present in them, such as emulsifiers, fatty substances, plant extracts, preservatives, perfumes, solvents, thickeners and preservatives in the customary amounts. The pH value of the cosmetic inflammation-inhibiting compositions for the care of the skin may be in the acid to neutral region (pH of 5 to 7.0) and is approximately adjusted to weakly acid values of about pH 6.

The present invention will now be further described by way of the following examples, but without limiting the invention to these examples.

EXAMPLES

The manufacture of the alkoxybenzoic acid esters, to be used in accordance with the present invention, will be described.

Compound A - n-Propyl Anisate 230 gm (1.32 mol) of anisoyl chloride were added drop by drop under agitation and cooling to a mixture of 316 gm (5.28 mol) of n-propanol and 300 ml of pyridine. The mixture was subsequently heated to 110° C. for three hours and then poured into a mixture of ice/water. The product was neutralized under cooling with half concentrated hydrochloric acid and extracted with ether. After drying, the ether phase was evaporated and the residue was fractionally distilled. The n-propyl anisate obtained had the following values:

227 gm (89% of theory)
Boiling point 83° C. to 85° C./0.05 Torr
$n_D^{20}$ = 1.5198 (Beilstein 10, II, p. 97; b.p. 176° C./45 Torr)

Compound B - Methyl Anisate
Melting point = 48° C. (Beilstein 10, II, p. 95, 49° C.)
Compound C - Isopropyl Anisate
Boiling point 88° C./0.05 Torr, $n_D^{20}$ = 1.5128
(Beilstein 10, III, p. 307; $n_D^{20}$ + 1.5107)
Compound D - Butyl Anisate
Boiling point 121° C./0.9 Torr, $n_D^{20}$ = 1.5152
(Beilstein 10, II, p. 97; $n_D^{20}$ = 1.5141)
Compound E - Tert.-Butyl Anisate
Boiling point 104° C./1.0 Torr, $n_D^{20}$ = 1.5085
(Beilstein 10, III, p. 308; b.p. 162-162.5° C./2.5-3 Torr)
Compound F - 2,2-Dimethyl-propyl Anisate
Boiling point 115° C./0.8 Torr, $n_D^{20}$ = 1.5058
Compound G - Benzyl Anisate
Boiling point 164° C./0.7 Torr, $n_D^{20}$ = 1.5787
(Beilstein 10, III, p. 311; b.p. 150°-155° C./1.0 Torr)

The following details demonstrate the inflammation-inhibiting properties of the compounds to be used in accordance with the present invention, and their suitability for use in cosmetic preparations, particularly for cosmetic agents for protection against sunburn and for the treatment of sunburn.

The alkoxybenzoic acid esters, to be used in accordance with the present invention, were tested for their inflammation-inhibiting properties in the experiments described hereinafter. An orientating test of their toxicity was first carried out in order to be able to establish the test dosages for further experiments.

The edema of the rat's paw test, as described by F. Kemper in "Arzneimittelforschung" 10 (1960), p. 777, was used as a test for assessing the compounds with respect to their suitability for inhibiting inflammation. In order to produce the edema, 0.1 ml of 6% dextran solution was injected to a depth of approximately 5 mm between the second and third toe of the right hind paw of the test animals. While only the dextran solution was administered to the control test animals, the various test substances were injected or administered per os to the test animals in the quantities given in Table I thirty minutes before the test animals were injected with the dextran solution. The volume of the paws was determined by means of the electrical volume measuring device described in detail by Kemper & Amelin in "Zeitschrift fur die gesamte experimentelle Medizin" 131 (1958), p. 407.

The measurements were taken thirty minutes after the dextran solution injection. For the purpose of comparison, the left untreated paw was in each case measured at the said times. The amount of the swelling in animals which had been treated with the test substance and in non-treated animals thirty minutes after the dextran injection were used to calculate the degree of the inhibiting of the edema as a percentage of the swelling which occurred in animals which had not received any test substance.

The so-called amputation methodology, described by C. H. Winter in Journal of Pharmaceutical and Experimental Therapeutics, Vol. 141 (1963), page 369, was used as a further rat's paw test. In this method, the test animals are killed three hours after injecting the substance causing the inflammation, and the weights of the paws are ascertained. The product used to cause inflammation in these tests is carrageenin. The inhibiting of the development of the edema of the rats' paws by the test substance, which was administered orally one hour before initiating the inflammation, serves as an indication of the efficacy and is expressed in percentages.

Based on general experience, the results of the rat's paw tests can serve as a basis for assessing a compound used as an agent for treating sunburn.

However, an ultraviolet test was carried out on hairless mice which also provide information concerning the efficacy of the substances for use as agents for treating sunburn. The backs of the hairless mice were exposed to radiation by an ultraviolet lamp for thirty minutes from a distance of 60 cm, thus causing a cutaneous inflammation. The test substances were administered to the test animals by interperitoneal injection or per os following the radiation, while the control test animals did not receive any after-treatment. The dosage of the test substances was the same as in the rat's paw test. The degree of formation of edema was determined by measuring the skin fold thickness after thirty hours. The degree of the percentage inhibition of the erythema is given in the following Table I and was determined by comparing the change in the skin fold thickness, caused in treated test animals by exposure to radiation, with the change in the skin fold thickness in animals which, although exposed to radiation, had not been treated.

Guinea pigs were subjected to the ultraviolet erythema test in a further experiment. For this purpose, the hair was removed from the backs of the test animals by shearing and treatment with a depilatory cream. The test animals were then exposed to radiation for eight minutes, and the marked test areas were then treated with the test solutions or salves. A second application was effected after thirty minutes, and a third and the following treatments were effected at intervals of sixty minutes. Six hours after having been exposed to radiation, the animals were washed, dried and visually assessed.

Assessment was repeated the following morning and the mean value for each substance was calculated from the two assessments. The two spots exposed to radiation directly behind the ears were chosen as reference points which had been exposed to radiation and which had not been treated. The intensity of the redness of these spots was equated with 0. Disappearance of the redness at the treated places was assessed by plus points up to +4 (no spots visible), and an intensification of the redness was assessed with minus points up to −4 (formation of blisters). The total of the assessments from the two evaluations, expressed in the ratio to the number of animals times 8 as the maximum attainable value (= 100%) gives the percentage inhibiting value of the substance. The inhibiting values ascertained in this manner are given in the following table under the heading "UR Erythema Guinea Pigs".

The values given in the following Table I were ascertained for the individual substances in the experiments which were carried out in the manner described above.

TABLE I

| | | Inflammation-Inhibiting Properties and Orientating Toxicity | | | | | |
|---|---|---|---|---|---|---|---|
| | | Rat's Paw Test | | | | | |
| Test Alkoxy- | | Carrageenin Edema | | Dextran Edema | | UV Edema in Hairless Mouse | UV Erythema in Guinea Pig |
| benzoic Acid Esters | Orientating Toxicity (gm/kg) | Dose (p.o.) (mg/kg) | Inhibition % | Dose (p.o.) (mg/kg) | Inhibition % | 5% in Vaseline® Inhibition After 30 hrs (%) | 5% Tincture Inhibition (%) |
| A | >1.0 | 1000 | 12 | 1000 | 25 | 49 | 60 |
| B | >1.0 | 1000 | 18 | 1000 | 28 | 41 | 31 |
| C | >1.0 | 1000 | 9 | 1000 | 20 | 38 | 40 |
| D | >1.0 | 1000 | 11 | 1000 | 9 | 36 | 51 |
| E | >1.0 | 1000 | 41 | 1000 | 11 | 30 | 43 |
| F | >1.0 | 1000 | 30 | 1000 | 15 | 35 | 48 |
| G | >1.0 | 1000 | 19 | 1000 | 5 | 31 | 46 | p.o. = per os (orally)

Some examples of cosmetic preparations, containing substances in accordance with the present invention, are given hereinafter.

EXAMPLE 1

For the purpose of producing an oil for protection against the sun, 20 gm of n-propyl anisate and 30 gm of menthyl salicylate were finely suspended in 100 gm of paraffin oil while heating and were then intimately mixed at approximately 25° C. with the following further constituents:
 300 gm of vegetable oil containing lecithin
 400 gm of olive oil
 100 gm of isopropyl myristate
 100 gm of purcellin oil.

EXAMPLE 2

In order to manufacture a sunburn powder, 40 gm of methyl anisate were intensively and homogenously distributed in:
 400 gm of rice starch
 400 gm of colloidal clay
 100 gm of lycopodium
 100 gm of talc
in a powder mixer.

EXAMPLE 3

In order to manufacture an inflammation-inhibiting after-shave lotion, 30 gm of 2,2-dimethyl-propyl anisate together with a solution of 5 gm of citric acid, 30 gm of glycerin in 100 gm of a tincture of witch hazel were made up to a total of 1000 gm with a perfumed 80% ethanol in water preparation.

EXAMPLE 4

In order to manufacture a cream for protection against the sun,
 40 gm of glycerin monostearate
 160 gm of beeswax
 420 gm of mineral oil
 50 gm of ceresine
 50 gm of an absorption base based on cholesterol, beeswax, stearyl alcohol and Vaseline$^R$
 30 gm of butyl anisate
 40 gm of benzyl salicylate
were melted together at 65° C. A mixture, heated to the same temperature, of
 247 gm of water
 13 gm of borax
 2 gm of methyl p-hydroxybenzoate
was incorporated into the aforesaid hot mixture under vigorous agitation, and the cream obtained was further agitated as it cooled to room temperature.

EXAMPLE 5

For the purpose of manufacturing an emulsion for protection against the sun, a mixture of 800 gm of water, 10 gm of glycerine and 9 gm of triethanolamine was added under violent agitation to a mixture, heated to approximately 80° C., of
 20 gm of glycerin monostearate
 70 gm of stearic acid
 30 gm of oleic acid
 20 gm of cetyl alcohol
 40 gm of benzyl anisate
 40 gm of 2-ethyl-hexyl p-methoxy-cinnamate.
The lotion obtained was subsequently agitated as it cooled to room temperature.

The above emulsion can also be packed in the form of an aerosol with the joint use of a propellant gas in the ratio of 80 parts of lotion to 20 parts of propellant gas.

Each of the alkoxybenzoic acid esters used in the above formulations can be replaced, with the same satisfactory result, by the other alkoxybenzoic acid esters mentioned above.

It is to be understood that the cosmetic preparations of oils, water-in-oil emulsions, oil-in-water emulsions, mixed aqueous water-soluble lower alkanol solutions having at least 20% lower alkanols and cosmetic powders, do not include simple solutions of the alkoxybenzoic acid esters in water which would not be classified as a cosmetic preparation.

The preceding specific embodiments are illustrative of the practice of the invention. It is to be understood, however, that other expedients known to those skilled in the art or disclosed herein, may be employed without departing from the spirit of the invention or the scope of the appended claims.

We claim:

1. A process for the care of the skin of warm-blooded animals against topical inflammation from sunburn comprising topically applying to the skin a safe but effective amount for the inhibiting of inflammation from sunburn of an alkoxybenzoic acid ester of the formula

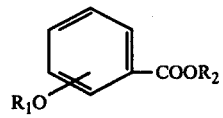

wherein $R_1$ is alkyl having 1 to 6 carbon atoms and $R_2$ is a member selected from the group consisting of alkyl having 1 to 8 carbon atoms, cyclohexyl, phenyl and benzyl, as an inflammation inhibitor.

2. The process of claim 1 wherein said alkoxybenzoic acid ester is present in an amount of from 0.01% to 10% by weight in a topical preparation selected from the group consisting of oils, water-in-oil emulsions, oil-in-water emulsions, mixed aqueous water-soluble lower alkanol solutions having at least 20% of lower alkanols, and topical powders.

3. The process of claim 2 wherein said alkoxybenzoic acid ester is present in said topical preparation in an amount of from 0.5% to 5% by weight.